(12) United States Patent
Griffin

(10) Patent No.: US 8,073,297 B2
(45) Date of Patent: Dec. 6, 2011

(54) SIDE FIRE OPTICAL DEVICE FOR LATERALLY REDIRECTING HIGH POWER ELECTROMAGNETIC ENERGY

(75) Inventor: Stephen E. Griffin, Peoria, AZ (US)

(73) Assignee: AMS Research Corporation, Minnetonka, MN (US)

( * ) Notice: Subject to any disclaimer, the term of this patent is extended or adjusted under 35 U.S.C. 154(b) by 248 days.

(21) Appl. No.: 12/517,879

(22) PCT Filed: Dec. 6, 2007

(86) PCT No.: PCT/US2007/024963
§ 371 (c)(1),
(2), (4) Date: Jun. 22, 2009

(87) PCT Pub. No.: WO2008/073263
PCT Pub. Date: Jun. 19, 2008

(65) Prior Publication Data
US 2011/0038580 A1  Feb. 17, 2011

Related U.S. Application Data

(60) Provisional application No. 60/869,007, filed on Dec. 7, 2006, provisional application No. 60/869,013, filed on Dec. 7, 2006.

(51) Int. Cl.
G02B 6/32 (2006.01)
B23P 11/00 (2006.01)
A61B 5/00 (2006.01)
A61B 18/18 (2006.01)

(52) U.S. Cl. ............. 385/33; 385/38; 385/96; 385/119; 29/428; 600/310; 606/16; 606/17; 606/18

(58) Field of Classification Search ............... 385/38, 385/27, 31, 36, 39, 47, 117, 118, 116, 119, 385/134, 146, 901, 96, 33; 29/428; 600/310, 600/327, 332, 339, 341, 342; 606/16, 17, 606/18
See application file for complete search history.

(56) References Cited

U.S. PATENT DOCUMENTS
4,669,467 A  6/1987  Willett et al. ............. 128/303.1
(Continued)

FOREIGN PATENT DOCUMENTS
EP  0689797 A1  6/1995
(Continued)

OTHER PUBLICATIONS

International Search Report and Written Opinion of PCT/US2007/024964 filed Dec. 6, 2007.
(Continued)

*Primary Examiner* — Brian Healy
(74) *Attorney, Agent, or Firm* — Westman, Champlin & Kelly, P.A.

(57) ABSTRACT

A side fire optical device comprises a cap member, a sleeve and a fiber optic segment. The cap member comprises a closed end section, a tube section having a bore, and a transmitting surface. The sleeve is received within the bore of the tube section. The sleeve includes a bore and an exterior surface that is fused to a surface of the bore of the cap member. The fiber optic segment comprises an exterior surface that is fused to a surface of the bore of the sleeve, and a beveled end surface that is positioned adjacent the transmitting surface of the cap member. The beveled end surface is angled relative to a longitudinal axis of the fiber optic segment such that electromagnetic radiation propagating along the longitudinal axis of the fiber optic segment is reflected by the beveled end surface at an angle that is transverse to the longitudinal axis and through the transmitting surface of the cap member.

24 Claims, 6 Drawing Sheets

U.S. PATENT DOCUMENTS

| | | | |
|---|---|---|---|
| 4,672,961 A | 6/1987 | Davies | 128/303.1 |
| 4,732,448 A * | 3/1988 | Goldenberg | 385/33 |
| 4,740,047 A | 4/1988 | Abe et al. | 385/39 X |
| 5,061,265 A | 10/1991 | Abela et al. | |
| 5,074,632 A | 12/1991 | Potter | 385/31 |
| 5,269,777 A | 12/1993 | Doiron et al. | 606/7 |
| 5,292,320 A | 3/1994 | Brown et al. | 606/18 |
| 5,343,543 A | 8/1994 | Novak, Jr. et al. | 385/31 |
| 5,354,294 A | 10/1994 | Chou | 606/16 |
| 5,428,699 A | 6/1995 | Pon | 385/31 |
| 5,486,171 A | 1/1996 | Chou | 606/16 |
| 5,495,541 A | 2/1996 | Murray et al. | 385/33 |
| 5,496,307 A | 3/1996 | Daikuzono | 606/15 |
| 5,496,308 A | 3/1996 | Brown et al. | 606/15 |
| 5,498,260 A | 3/1996 | Rink et al. | 106/19 B |
| 5,509,917 A | 4/1996 | Cecchetti et al. | 606/15 |
| 5,512,078 A | 4/1996 | Griffin | 65/484 |
| 5,530,780 A | 6/1996 | Ohsawa | 385/31 |
| 5,537,499 A | 7/1996 | Brekke | 385/31 |
| 5,562,657 A | 10/1996 | Griffin | 606/17 |
| 5,571,099 A | 11/1996 | Purcell, Jr. et al. | 606/17 |
| 5,695,583 A | 12/1997 | van den Bergh et al. | 156/153 |
| 5,807,390 A | 9/1998 | Fuller et al. | 606/17 |
| 5,824,005 A | 10/1998 | Motamedi et al. | 606/15 |
| 6,246,817 B1 | 6/2001 | Griffin | 385/43 |
| 6,270,492 B1 | 8/2001 | Sinofsky | 606/15 |
| 6,284,085 B1 | 9/2001 | Gwo | 156/273.7 |
| 6,398,778 B1 | 6/2002 | Gu et al. | 606/15 |
| 6,522,806 B1 | 2/2003 | James, IV et al. | 385/31 |
| 6,687,436 B2 * | 2/2004 | Griffin | 385/43 |
| 6,712,526 B1 * | 3/2004 | Fleenor | 385/78 |
| 6,829,411 B2 | 12/2004 | Easley | 385/31 |
| 6,986,764 B2 | 1/2006 | Davenport et al. | 606/3 |
| 7,909,817 B2 * | 3/2011 | Griffin et al. | 606/13 |
| 2005/0165279 A1 | 7/2005 | Adler et al. | 600/181 |
| 2006/0291061 A1 | 12/2006 | Iyama et al. | 359/614 |
| 2007/0106286 A1 * | 5/2007 | Harschack et al. | 606/17 |
| 2008/0287936 A1 | 11/2008 | Stinson et al. | 606/13 |
| 2010/0135617 A1 | 6/2010 | Novak, Jr. et al. | 385/77 |
| 2011/0038580 A1 * | 2/2011 | Griffin | 385/33 |

FOREIGN PATENT DOCUMENTS

| | | |
|---|---|---|
| JP | 60250322 | 12/1985 |
| JP | 62011820 | 1/1987 |
| JP | 03111040 | 5/1991 |
| JP | 0 689 797 A1 | 6/1995 |
| JP | 10155805 | 6/1998 |
| JP | 2001346891 | 12/2001 |
| WO | 2008073263 A1 | 6/2008 |
| WO | 2008073264 A2 | 6/2008 |

OTHER PUBLICATIONS

U.S. Appl. 12/517,883, filed Jun. 5, 2009.
U.S. Appl. No. 61/118,857, filed Dec. 1, 2008.
International Search Report and Written Opinion of PCT/US2007/024963 filed Dec. 6, 2007.

* cited by examiner

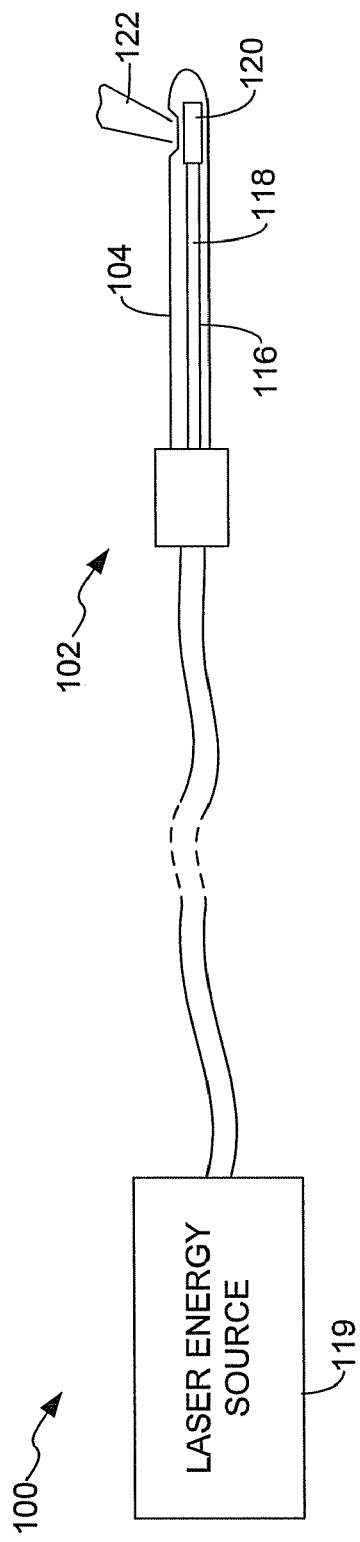
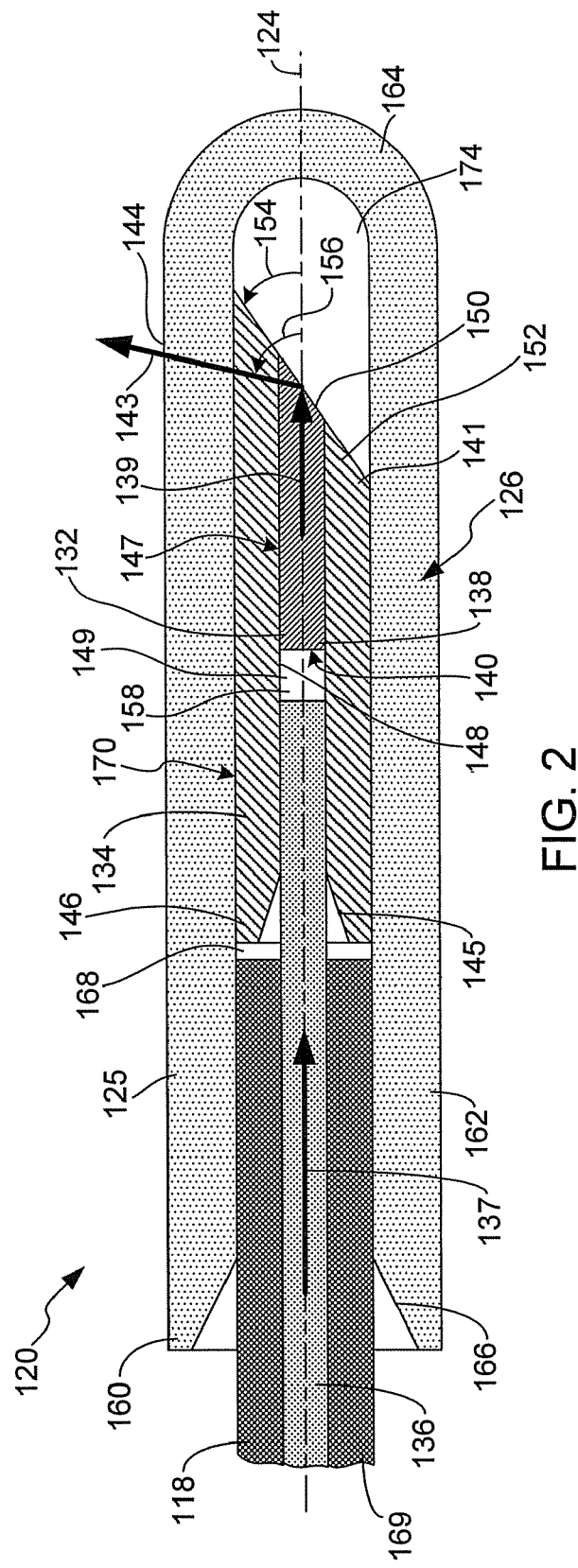
FIG. 1
FIG. 2

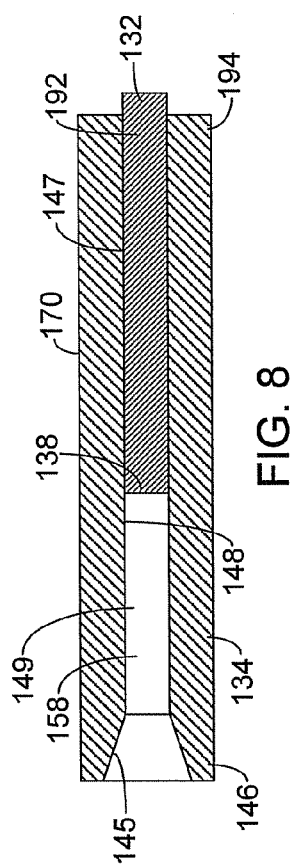
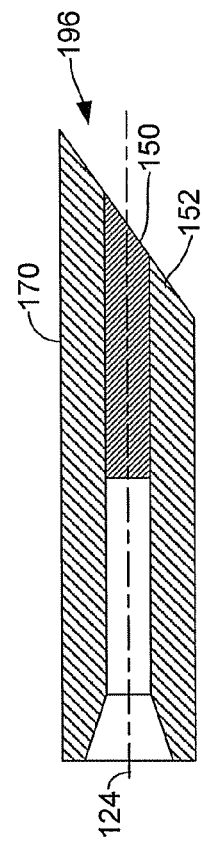
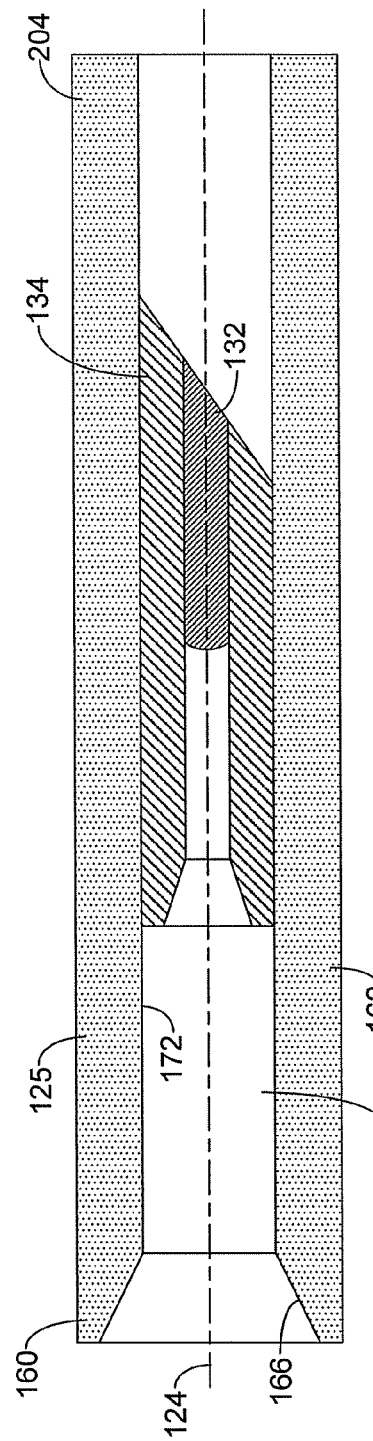
FIG. 8
FIG. 9
FIG. 10

_US 8,073,297 B2_

SIDE FIRE OPTICAL DEVICE FOR LATERALLY REDIRECTING HIGH POWER ELECTROMAGNETIC ENERGY

CROSS-REFERENCE TO RELATED APPLICATION

This application is a Section 371 National Stage Application of International Application No. PCT/US2007/024963, filed Dec. 6, 2007 and published as WO 2008/073263 A1 on Jun. 19, 2008, and claims the benefit of U.S. Provisional Application Ser. No. 60/869,007 filed Dec. 7, 2006 and U.S. Provisional Application Ser. No. 60/869,013 filed Dec. 7, 2006 under 35 U.S.C. §119(e). Each of the above-referenced applications are incorporated herein by reference in their entirety.

BACKGROUND

Electromagnetic energy, such as laser light, is used to perform various medical procedures including the destruction of cancerous tissues, for example. One optical device that is used in surgical tools that perform such medical procedures is a side fire optical device.

Side fire optical devices are typically used to redirect delivered electromagnetic radiation (hereinafter "laser light") in an off-axis direction from the longitudinal axis of the delivery fiber and the device, typically at and angle of 74-76 degrees off axis. Conventional side fire optical devices operate by reflecting the electromagnetic radiation off of a beveled optical surface. The redirected output laser light is transmitted through a transmitting surface of the device to the surgical site. One exemplary side-firing optical device is disclosed in U.S. Pat. No. 5,428,699.

During surgery, components of side fire optical devices, such as the surface of the external cap, rapidly heat and cool. This thermal cycling produces large stresses in the in the components of the side fire optical device. The thermal cycling of components of the device is magnified along with the stresses in the components, when high power lasers (e.g., 100 W holmium laser energy, 120 W 532 nm laser energy, etc.) are utilized and further magnified when the device is involved in tissue contact surgery. The stresses in the side fire optical devices often cause components of the device to crack or, even worse, shatter.

SUMMARY

Embodiments of the present invention are directed to a side fire optical device for laterally redirecting electromagnetic radiation. In one embodiment, the device includes a cap member, a sleeve and a fiber optic segment. The cap member comprises a closed end section, a tube section having a bore, and a transmitting surface. The sleeve is received within the bore of the tube section. The sleeve includes a bore and an exterior surface that is fused to a surface of the bore of the cap member. The fiber optic segment comprises an exterior surface that is fused to a surface of the bore of the sleeve, and a beveled end surface that is positioned adjacent the transmitting surface of the cap member. The beveled end surface is angled relative to a longitudinal axis of the fiber optic segment such that electromagnetic radiation propagating along the longitudinal axis of the fiber optic segment is reflected by the beveled end surface at an angle that is transverse to the longitudinal axis and through the to transmitting surface of the cap member.

Another embodiment of the invention is directed to a method of manufacturing a side fire optical device for laterally redirecting electromagnetic radiation. In one embodiment of the method, a fiber optic segment is inserted into a bore of a sleeve. An exterior surface of the fiber optic segment is fused to an interior surface of the bore of the sleeve. A reflecting end of the fiber optic segment is beveled to form a beveled end surface that is angled relative to a longitudinal axis of the fiber optic segment such that electromagnetic radiation propagating along the longitudinal axis of the fiber optic segment is reflected by the beveled end surface at an angle that is transverse to the longitudinal axis. The sleeve and fiber optic segment are inserted into a tube section of a cap member. An exterior surface of the sleeve is fused to an interior surface of a bore of the tube section and an end of the tube section is closed that is adjacent the beveled end surface. In one embodiment, the fused fiber optic segment, sleeve and cap member are annealed.

This Summary is provided to introduce a selection of concepts in a simplified foam that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

FIG. 1 is a simplified diagram of an exemplary laser surgical system and surgical tool in accordance with embodiments of the invention.

FIG. 2 is a side cross-sectional view of a side fire optical device in accordance with embodiments of the invention.

FIGS. 8-10 are side cross-sectional view of various stages of manufacture of a side fire optical device in accordance with embodiments of the invention.

DETAILED DESCRIPTION OF ILLUSTRATIVE EMBODIMENTS

Figure 3:
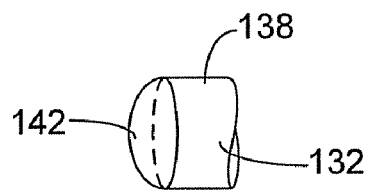
FIG. 3 is a magnified isometric view of a receiving end of a fiber optic segment in accordance with embodiments of the invention.

FIG. 1 is a simplified diagram of an exemplary laser surgical system 100 in accordance with embodiments of the invention. The system 100 includes a surgical tool 102, in which embodiments of the present invention are useful. The surgical tool 102 includes an outer sheath 104. The surgical tool 102 can be used to perform medical procedures in which tissues of a surgical site of a patient are exposed to electromagnetic radiation, preferably in the form of laser light, such as in the treatment of an enlarged prostate gland. The outer sheath 104 can be formed of series 300 stainless steel or other suitable material, such as aluminum, thermal plastics, or other materials. The outer sheath 104 has a circular cross-section with a diameter sufficient to support the components of the surgical tool 104.

A cannula 110, having a circular cross-section, is positioned within the sheath 104. A probe 116 is provided in the cannula 110. The probe 116 includes a delivery fiber optic 118 for communicating or transmitting electromagnetic radiation from a source, such as laser energy source 119, to a side fire optical device or fiber optic cap 120, which is formed in accordance with embodiments of the invention described below. The side fire optical device 120 redirects the electromagnetic radiation (hereinafter "laser light") transmitted by the fiber optic 118 laterally or transverse to a longitudinal axis of the probe 116 onto the surgical site, as illustrated by laser light 122 in FIG. 1.

The surgical tool 102 may also include a saline inflatable balloon configured to secure the position of the probe 116 at the surgical site and for other purposes known in the art. Additionally, the surgical tool 102 may include a scope for viewing the surgical site.

FIG. 2 is a side cross-sectional view of the side fire optical device 120 in accordance with embodiments of the invention. The components of the side fire optical device 120 preferably have a cylindrical shape. That is, cross-sections of the components of the side fire optical device 120 taken in a plane that is perpendicular to a longitudinal axis 124 of the device 120 are generally circular. However, it should be understood that the individual components of the side fire optical device 120 can take on other non-circular cross-sectional shapes in the plane that is perpendicular to the longitudinal axis 124.

One embodiment of the device 120 comprises a cap member 125 and a redirecting element 126 that is received within the cap member 125. The redirecting element 126 comprises a fiber optic segment 132 and a sleeve 134.

In one embodiment, the fiber optic segment 132, the sleeve 134 and the cap member 125 are each formed substantially (i.e., entirely, or nearly entirely) of silica. The water content of the silica used to form the fiber optic segment 132 and the sleeve 134 may be selected based on the wavelength of the laser light generated by the laser energy source 119. The formation of the components of the device 120 of silica allows the device 120 to be annealed after the components are fused together, which relieves the device 120 of residual strains that develop during the various fusion processes. The resultant side fire optical device 120 is better capable of handling high power electromagnetic radiation (e.g., 100 W holmium laser energy) than side fire optical devices of the prior art utilizing caps that are fused to other components of the device because such devices cannot be annealed to relieve residual stresses in the fused silica components due to their use of polymers. Additionally, the side fire optical device 120 is better capable of handling high power electromagnetic radiation than side fire optical devices of the prior art that do not utilize a cap that is fused to other components of the device, which tend to break down at the surface of the cap.

The fiber optic segment 132 can have a diameter that is the same as, smaller than, or larger than the delivery core fiber 136 of the fiber optic 118. In one embodiment, the length of the fiber optic segment 132 is less than 1 cm. In other embodiments, the fiber optic segment 132 has a length that is within in the range of 0.1 to 2.0 cm, such as 1.0 cm. Laser light signals 137, delivered from the fiber 136, are received at a receiving end 138 of the fiber optic segment 132. The received laser light signals 139 propagate along the longitudinal axis 124 of the segment 132.

In one embodiment, the receiving end 138 comprises a flat polished surface 140, which is perpendicular to the longitudinal axis 124. In another embodiment, the receiving end 138 comprises a lens 142, as shown in FIG. 3, which is a magnified isometric view of the receiving end 138 of the fiber optic segment 132. Additionally, the transmitting fiber 136 may be equipped with a terminal lens, similar to or of different curvature than that on the receiving end 138 of the fiber segment 132. The lenses are preferably configured to facilitate efficient coupling between the delivery core fiber 136 and the fiber optic segment 132, provide a mechanism for controlling the output of the redirected laser light signal 143 through a transmitting surface 144 of the cap member 125, and/or perform other functions. One exemplary lens 142 is a convex lens as illustrated in FIG. 3.

As mentioned above, one embodiment of the sleeve 134 is formed of silica. However, other embodiments include the use of other materials that are either the same or different than that of the fiber optic segment 132. In one embodiment, the sleeve 134 is a cylindrical member that receives the short fiber optic segment 132 within a central bore 149 that has a diameter that is only slightly larger than the diameter of the fiber optic segment 132. In one embodiment, a chamfer 145 is formed at a receiving end 146 of the sleeve 134, which is opposite a transmitting end 141. The chamfer 145 forms a chamfered opening to the bore 149. The chamfer 145 can be sized to facilitate the receipt of the delivery core fiber 136 of the fiber optic 118, such that the core fiber 136 is urged into substantially coaxial alignment with the fiber optic segment 132.

In one embodiment, an exterior surface 147 of the fiber optic segment 132 is fused to the interior surface 148 of the bore 149 of the sleeve 134. Preferably, in this embodiment, the fiber optic segment 132 and the sleeve 134 are each entirely formed of silica. Exemplary methods of fusing the fiber optic segment 132 to the sleeve 134 are discussed below.

The fiber optic segment 132 includes a beveled end surface 150 that is positioned adjacent to the transmitting surface 144 of the cap member 125, as shown in FIG. 2. In one embodiment, the sleeve 134 comprises a beveled end surface 152 that is coplanar to the beveled end surface 150. The interior side of the beveled end surface 150 forms an optical surface that reflects or redirects the laser light signals 139 received from the delivery core fiber 136. The beveled end surface 150 is oriented at an angle 154 relative to the longitudinal axis 124. The angle 154 is selected, in accordance with conventional methods, to provide substantially total internal reflection of the laser light signals 139 propagating along the longitudinal axis 124, such that the laser light signals 139 are redirected laterally through the transmitting surface 144, as illustrated by signals 143. The angle 154 is typically in the range of 37-38 degrees. The angle 156 to which the light signals 137 are redirected (signals 143) relative to the longitudinal axis 124 is generally twice the angle 154, or approximately 74-76 degrees off the longitudinal or fiber axis 124.

In one embodiment, the receiving end 138 of the fiber optic segment 132 is displaced along the longitudinal axis 124 from the receiving end 146 of the sleeve 134, as shown in FIG. 2. That is, a gap 158 is formed between the receiving end 146 of the sleeve 134 and the receiving end 138 of the fiber optic segment 132. The gap 158 can be selected to control the properties of the laterally redirected light signal 143, particularly when the receiving end 138 of the fiber optic segment 132 includes a lens 142 as shown in FIG. 3.

Figure 4:
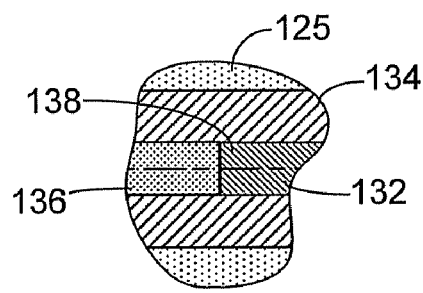
FIG. 4 is a partial side cross-sectional view of the side fire optical device of FIG. 2 illustrating the optical coupling of a fiber optic segment of the device to a delivery core fiber, in accordance with an embodiment of the invention.

In accordance with another embodiment, the receiving end 138 of the fiber optic segment 132 is positioned at the receiving end 146 of the sleeve 134, as illustrated in the partial cross-sectional view of the device 120 provided in FIG. 4. In one embodiment, the receiving end 138 of the fiber optic segment 132 is positioned within the sleeve 134 such that the receiving end 138 abuts, or is in close proximity to, the delivery core fiber 136 when the device 120 is installed on the fiber optic 118.

One embodiment of the cap member 125 is substantially formed of silica, as mentioned above. The cap member 125 comprises a receiving end 160 a tube section 162 and a closed end section 164. One embodiment of the receiving end 160 includes a chamfer 166, which forms a chamfered opening to a bore 168 of the tube section 162. In one embodiment, the tube section 162 comprises a circular cross section in the plane extending perpendicular to the longitudinal axis 124. One embodiment of the bore 168 has an internal diameter that is sized to accommodate the delivery fiber optic 118 including the core fiber 136, the cladding, and the buffer coating 169. The chamfer 166 at the receiving end 160 assists in simplifying the insertion of the delivery fiber optic 118 into the bore 168.

The redirecting element 126 is received within the tube section 162 of the cap member 125, as shown in FIG. 2. In one embodiment, an exterior surface 170 of the sleeve 134 is fused to an interior surface 172 of the bore 168. In one embodiment, the bore 168 of the tube section 162, the bore 149 of the sleeve 134, and the fiber optic segment 132 are coaxial.

In one embodiment, the beveled end surface 150 of the fiber optic segment 132 is displaced from the interior walls of the cap member 125 due to the sleeve 134. Additionally, the beveled end surface 150 of the fiber optic segment 132 is displaced from the interior wall of the closed end 164. The closed end 164 and the beveled end surfaces 150 and 152 define an interior cavity 174 that is filled with air or a selected gas. The closed end 164 seals the interior cavity 174.

Figure 6:
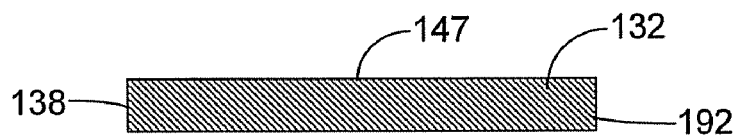
FIG. 6 is a side cross-sectional view of a fiber optic segment in accordance with an embodiment of the invention.
Figure 7:
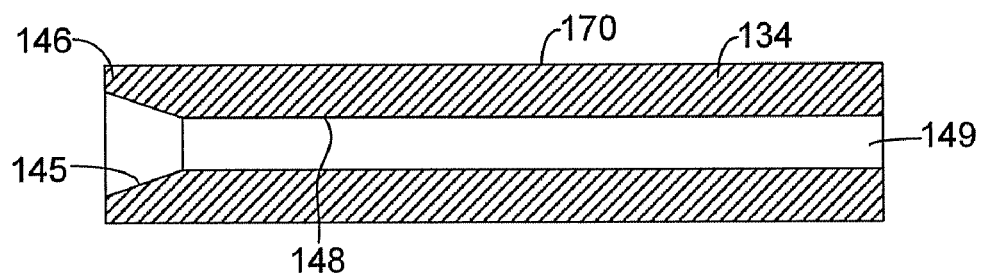
FIG. 7 is a side cross-sectional view of a sleeve in accordance with embodiments of the invention.
Figure 5:
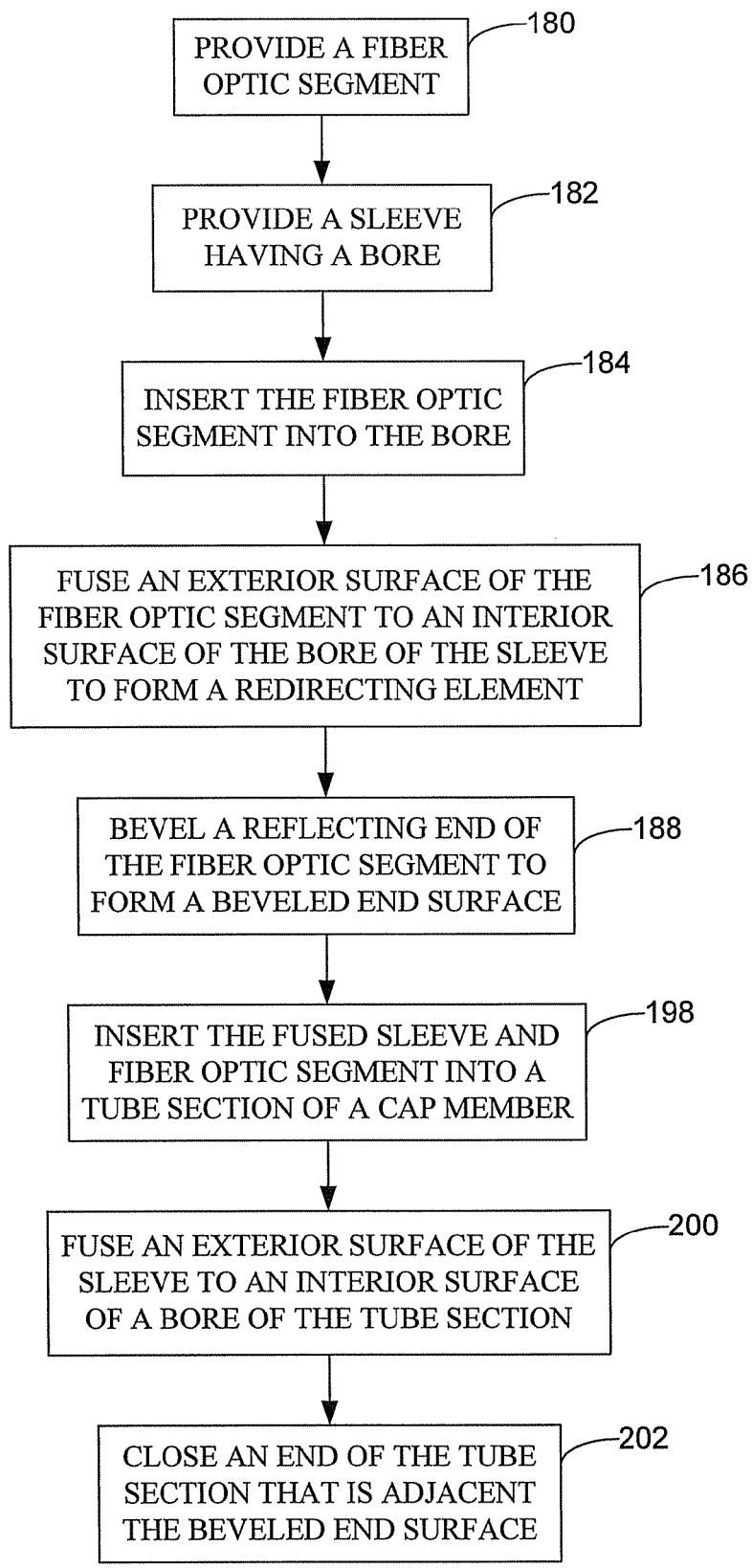
FIG. 5 is a flowchart illustrating a method of manufacturing a side fire optical device for laterally redirecting electromagnetic radiation is accordance with embodiments of the invention.

FIG. 5 is a flowchart illustrating a method of manufacturing embodiments of the side fire optical device 120 described above. Initially, at steps 180 and 182, a fiber optic segment 132 (FIG. 6) and a sleeve 134 (FIG. 7) are provided. The fiber optic segment 132 and the sleeve 134 can be formed in accordance with any of the embodiments described above. Initially, the fiber optic segment 132 is a straight section of fiber optic, as shown in FIG. 6. In one embodiment, the receiving end 138 of the fiber optic element 132 is either formed into a lens or a lens 142 is attached to the receiving end 138, as illustrated in FIG. 3. In one embodiment of the sleeve 134, a chamfer 145 is formed at the receiving end 146 to form a chamfered opening to the bore 149, as shown in FIG. 7.

At step 184, the fiber optic segment 132 is inserted into the bore 149 of the sleeve 134, as shown in FIG. 8. As mentioned above, the fiber optic segment 132 can be positioned within the bore 149 such that a gap 158 exists between the receiving end 146 of the sleeve 134 and the receiving end 138 of the fiber optic segment 132, as shown in FIG. 8. Alternatively, the receiving end 138 of the fiber optic segment 132 can be positioned to abut the receiving end 146 of the sleeve 134, as shown in FIG. 4.

At step 186, an exterior surface 147 of the fiber optic segment 132 is fused to an interior surface 148 of the bore 149. The fusion of the fiber optic segment 132 to the sleeve 134 can be accomplished using conventional techniques. In one such technique, the fiber optic segment 132 and the sleeve 134 are rotated under laser illumination. The laser is scanned down the sleeve 134 until fusion is accomplished. Other techniques to fuse the fiber optic segment 132 to the sleeve 134 include furnace fusion, low temperature glass melt and other conventional techniques.

At step 188, at least a reflecting end 192 of the fiber optic segment 132 is beveled to form a beveled end surface 150, as shown in FIG. 9. In one embodiment, the reflecting end 192 of the fiber optic segment 132 and the end 194 of the sleeve 134 are cut and polished using conventional techniques, such as mechanical polishing to form a bevel 196 in the fused component. Other suitable known techniques may also be used to form the bevel 196, e.g. laser cutting and polishing. In one embodiment, the bevel 196 comprises the beveled end surface 150 of the fiber optic segment 132 and the beveled end surface 152 of the sleeve 134 described above.

At step 198, the fused sleeve 134 and fiber optic segment 132 is inserted into a tube section 162 of a cap member 125, as shown in FIG. 10. Next, an exterior surface 170 of the sleeve 134 is fused to an interior surface 172 of a bore 168 of the tube section 162 at step 200. The techniques used to fuse the fiber optic segment 132 to the sleeve 134 can also be used to fuse the sleeve 134 to the tube section 162.

At step 202, an end 204 of the tube section 162 is closed to form the closed end 164 shown in FIG. 2. The closing of the end 204 of the tube section 162 can be accomplished using various known techniques. One such technique involves melting and collapsing the end 204 of the tube section 162 using a laser.

In accordance with one embodiment of the method, the assembled side fire optical device 120 is annealed at a temperature in excess of 1000 degrees Centigrade. This process relieves the stresses formed in the components of the side fire optical device 120 due to the fusion processes. Once annealed, the side fire optical device 120 becomes more capable of withstanding the redirecting of high powered electromagnetic radiation and rapid thermal cycling inherent in surgical use as compared to prior art electromagnetic radiation redirecting devices.

Figure 14:
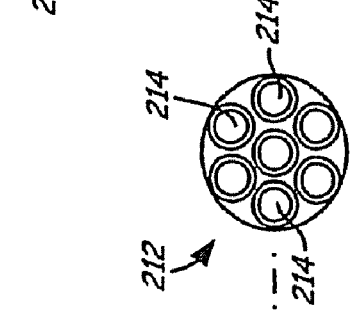
FIG. 14 is a front plan view of a fiber optic bundle in accordance with embodiments of the invention.
Figure 13:
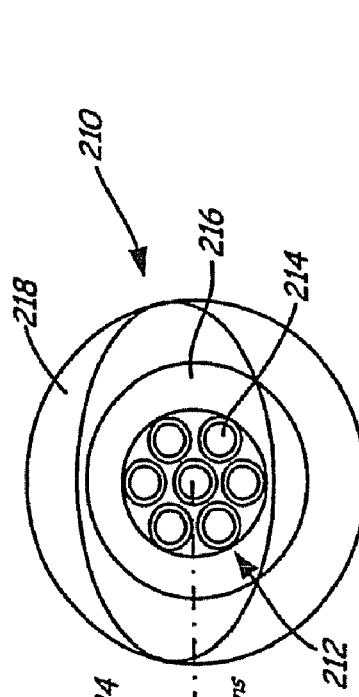
FIGS. 11-13 respectively show a top plan view, a side cross-sectional view and a front view of a multi-channel device for laterally redirecting electromagnetic energy from multiple fiber optics, in accordance with embodiments of the invention.
Figure 11:
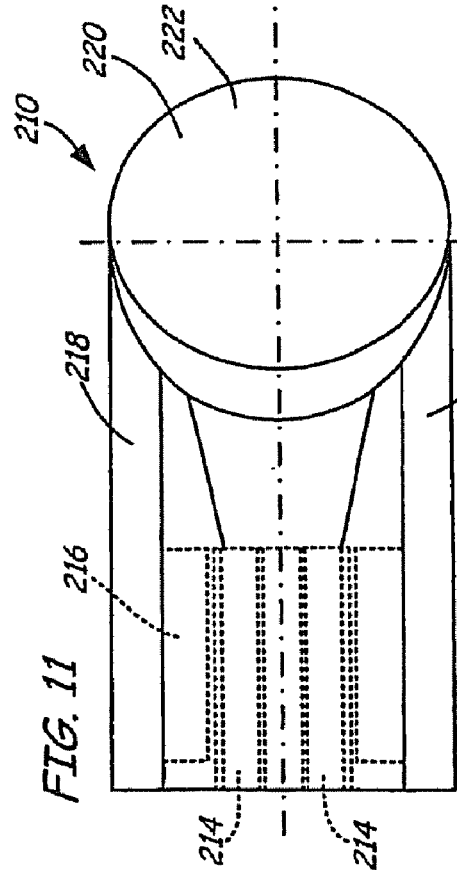
Figure 12:
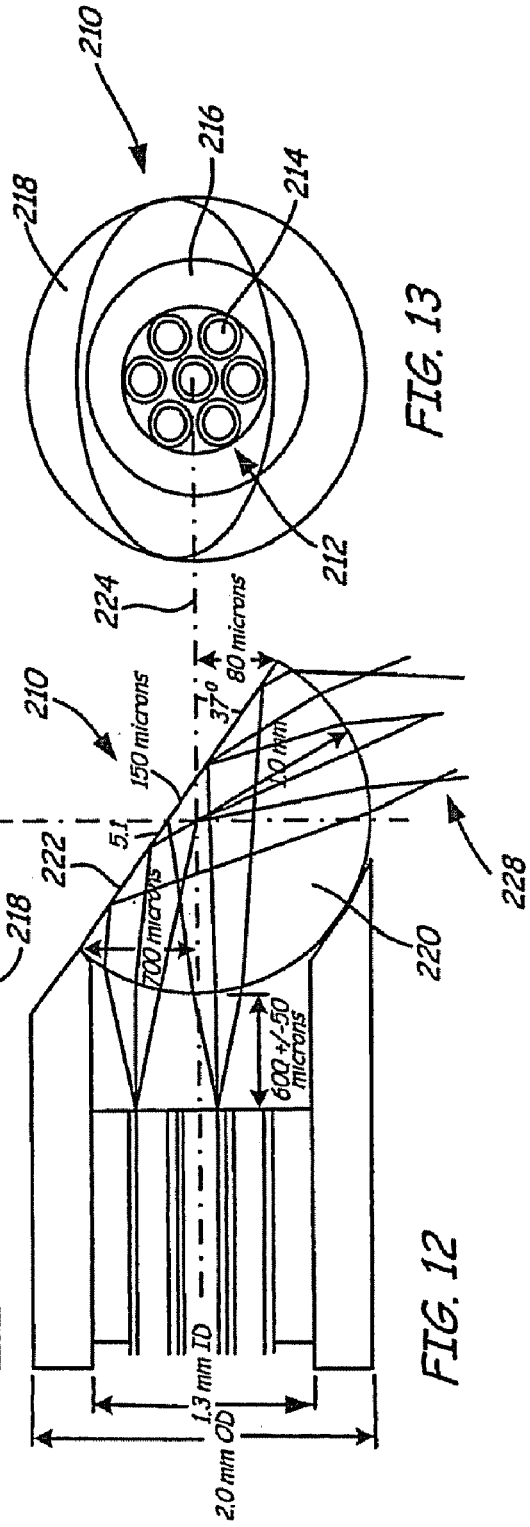

FIGS. 11-13 respectively show a top plan view, a side cross-sectional view and a front view of a multi-channel device for laterally redirecting electromagnetic energy from multiple fiber optics. in accordance with embodiments of the invention. The device 210 couples to a fiber optic bundle 212 (FIG. 14) comprising a plurality of individual fiber optics 214. In one embodiment, the fiber optic bundle 212 is received within a sleeve 216. The inner sleeve 216 is coupled to an outer sleeve 218 through fusion or other suitable coupling method. A ball lens 220 is fused to an open end of the sleeve 218. The ball lens 220 is cut and polished to faun a beveled end surface 222 that is angled relative to the longitudinal axis 224 of the sleeve 218 and the sleeve 216 such that the electromagnetic radiation (e.g., laser light) transmitted by one or more of the fiber optics 214 is coupled to the ball lens 220 and reflected off the interior side of the beveled end surface 222 and through a transmitting surface 226 of the ball lens 220, as illustrated by the exemplary light signal lines 228 in FIG. 12.

Figure 15:
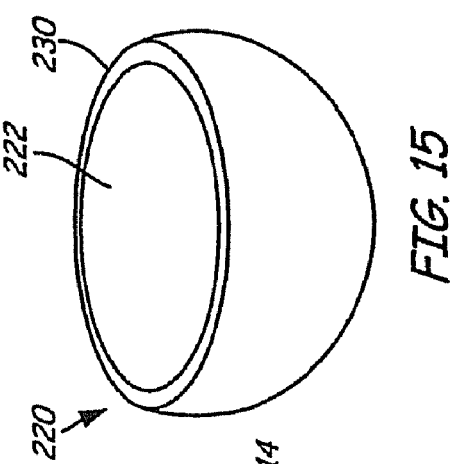
FIG. 15 is an isometric view of a ball lens in accordance with embodiments of the invention.
Figure 16:
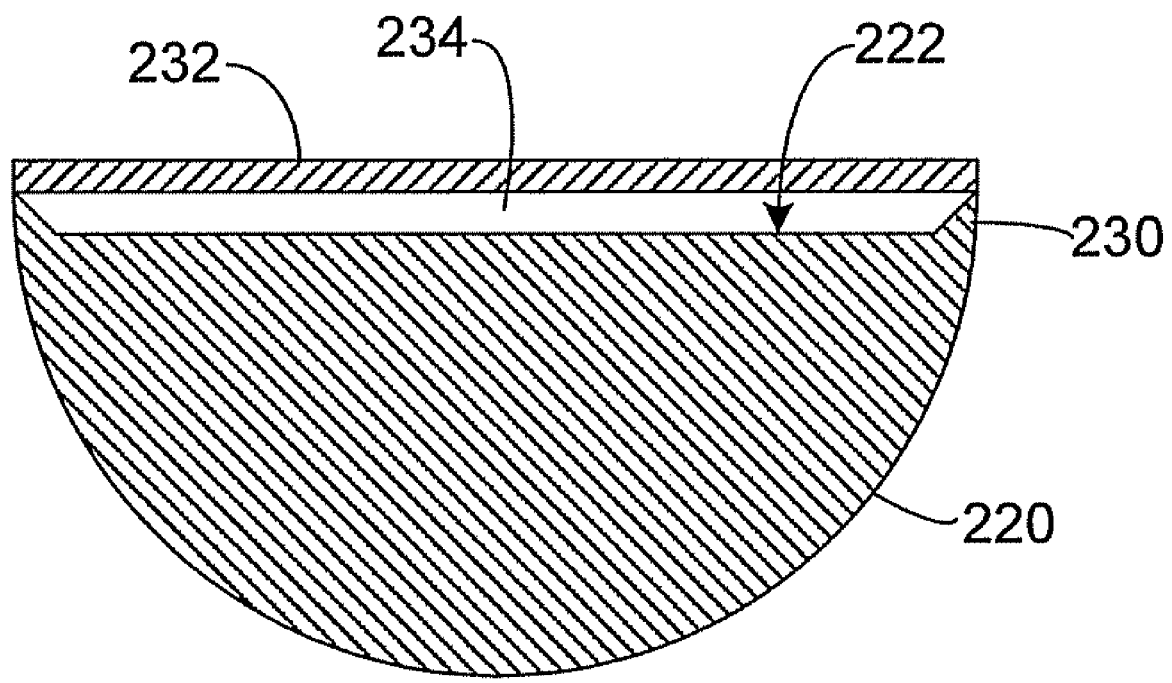
FIG. 16 is a cross-sectional view of a ball lens in accordance with an embodiment of the invention.

In one embodiment, the polished beveled end surface 222 is encapsulated to form an air interface at the surface 222. FIG. 15 is an isometric view of the ball lens 220 and FIG. 16 is a cross-sectional view of the ball lens 220 in accordance with one embodiment, in which a raised edge 230 is formed at the perimeter of the surface 222, as illustrated in FIG. 15. In one embodiment, the raise edge is approximately 20 microns higher than the surface 222. A thin sheet of glass 232 is then fused to the raised edge 230 and any access of the glass sheet 232 extending beyond the raised edge 230 is trimmed away. This results in the encapsulation of the beveled end surface 222 and leaves a thin film of air in the formed cavity 234 that interfaces with the end surface 222. As a result, the device 210 can laterally direct the electromagnetic radiation transmitted by the fiber optics 214 even when the device is in contact with liquid or other material that could affect the operation of the device 210.

In another embodiment, the fiber optic bundle 212 contains fiber optics 214 that are coupled to laser energy sources that generate laser light of different surgical wavelengths to allow the device 210 to be used to perform multiple procedures. For example, one fiber optic 214 may carry a surgical wavelength of laser light that is suitable to vaporize or fragment kidney stones while another fiber optic 214 transmits laser light having a surgical wavelength that is suitable for coagulation. In another embodiment, one of the fiber optics 214 carries laser light having a wavelength that is suitable for diffuse reflectance while one or more of the other fiber optics 214 are used to collect the reflectance for spectral analysis. As a result, the device 210 can be used to both analyze the tissues of the patient and treat those tissues without having to change devices. Thus, the device 210 can be configured to have one or more fiber optics 214 that can be used to provide optical screening for one or more cancers or other diseases and other fiber optics 214 that are configured to perform surgery.

In another embodiment, the device 210 may be used to locate and treat vulnerable plaque (a semi-fluid inclusion in the arterial wall that causes fatal heart attacks when it escapes) in coronary arteries. Here, one or more of the optical fibers 214 are connected to a rapidly tunable visible laser (e.g., 200 nm scan range). The laser light is delivered to the arterial wall through the device 210, which redirects the light to an arterial wall, which it penetrates. When it encounters vulnerable plaque the scattered laser light is altered in a manner that is detectable when delivered to a spectrometer by the surrounding fiber optics 214 of the device 210. If more than one ring of fibers 214 is used to collect the scattered light, different depths can be scanned, giving a low resolution "image" of the plaque profile. While this alone is of great value, one may also use other fiber optics 214 of the bundle 212 to deliver a surgical wavelength of laser light that can "cook" the vulnerable plaque and make it a solid material that can not escape through the artery wall.

In another embodiment, one of the fiber optics 214 of the device 210 is be used to deliver Raman excitation while other fiber optics 214 of the bundle 212 collects the florescence from prostate tissue. If the returned spectrum indicates cancerous tissue, other fiber optics 214 of the fiber optic bundle 212 that are not being used for spectroscopy can deliver surgical wavelengths of laser light to kill the cancerous tissue. As a result, the device 210 can be used to provide real-time targeting of deceased tissue while sparing healthy tissue.

Although the present invention has been described with reference to preferred embodiments, workers skilled in the art will recognize that changes may be made in form and detail without departing from the spirit and scope of the invention.

What is claimed is:

1. A side fire optical device for laterally redirecting electromagnetic radiation-comprising:
    a cap member comprising a closed end section, a tube section having a bore, and a transmitting surface;
    a sleeve received within the bore of the tube section, the sleeve including a bore and an exterior surface that is fused to a surface of the bore of the cap member; and
    a fiber optic segment comprising an exterior surface that is fused to a surface of the bore of the sleeve, a beveled end surface positioned adjacent the transmitting surface of the cap member and a receiving end opposite the beveled end surface that is within the bore of the tube section, wherein the beveled end surface is angled relative to a longitudinal axis of the fiber optic segment such that electromagnetic radiation propagating along the longitudinal axis of the fiber optic segment is reflected by the beveled end surface at an angle that is transverse to the longitudinal axis and through the transmitting surface of the cap member.

2. The device of claim 1, wherein the beveled end surface and the closed end of the cap member define an interior cavity.

3. The device of claim 1, wherein the sleeve, the fiber optic segment and the cap member are formed substantially of silica.

4. The device of claim 1, wherein the fiber optic segment comprises a lens attached to a receiving end of the fiber optic segment that is opposite the beveled end surface.

5. The device of claim 4, wherein the lens comprises a convex lens.

6. The device of claim 1, wherein:
    the receiving end of the fiber optic segment is within the bore of the sleeve; and
    the sleeve comprises a receiving end that is displaced along the longitudinal axis from the receiving end of the fiber optic segment and the beveled end surface.

7. The device of claim 6, wherein the receiving end of the sleeve comprises a chamfered opening to the bore of the sleeve.

8. The device of claim 1, wherein the fiber optic segment is less than 2.0 cm.

9. The device of claim 1, wherein the cap member comprises a receiving end that is opposite the closed end and comprises a chamfered opening to the bore of the tube section.

10. The device of claim 1, wherein the sleeve and the fiber optic segment are coaxial.

11. The device of claim 1, wherein the fused fiber optic segment, the sleeve and the cap member are annealed at a temperature of greater than 1000 degrees Centigrade.

12. The device of claim 1, wherein the sleeve comprises a beveled end surface that is coplanar to the beveled end surface of the fiber optic segment.

13. A side fire optical device formed of silica for laterally redirecting electromagnetic radiation comprising:
    a cap member comprising a closed end, a cylindrical tube section having a bore, and a transmitting surface;
    a cylindrical sleeve received within the tube section and comprising a bore, an exterior surface that is fused to a surface of the bore of the tube section, a receiving end and a transmitting end opposite the receiving end; and
    a fiber optic segment coaxial to the cylindrical sleeve and separated from the cap member, the fiber optic segment comprising an exterior surface that is fused to a surface of the bore of the cylindrical sleeve, a beveled end surface is positioned adjacent the transmitting surface, a receiving end opposite the beveled end surface, and a gap between the receiving end of the cylindrical sleeve and the receiving end of the fiber optic segment, wherein the beveled end surface is angled relative to a longitudinal axis of the fiber optic segment such that electromagnetic radiation propagating along the longitudinal axis of the fiber optic segment is reflected by the beveled end surface at an angle that is transverse to the longitudinal axis and through the transmitting surface of the cap member.

14. The device of claim 13, wherein: the fiber optic segment comprises a lens attached to the receiving end of the fiber optic segment.

15. The device of claim 13, wherein the receiving end of the sleeve comprises a chamfered opening to the bore of the sleeve.

16. The device of claim 13, wherein the cap member comprises a receiving end that is opposite the closed end and comprises a chamfered opening to the bore of the tube section.

17. The device of claim 13, wherein the fused fiber optic segment, sleeve and cap member are annealed at a temperature of greater than 1000 degrees Centigrade.

18. The device of claim 13, wherein the sleeve comprises a beveled end surface that is coplanar to the beveled end surface of the fiber optic segment.

19. A method of manufacturing a side fire optical device for laterally redirecting electromagnetic radiation, the method comprising:
   inserting a fiber optic segment into a bore of a sleeve;
   fusing an exterior surface of the fiber optic segment to an interior surface of the bore of the sleeve;
   beveling a reflecting end of the fiber optic segment to form a beveled end surface that is angled relative to a longitudinal axis of the fiber optic segment such that electromagnetic radiation propagating along the longitudinal axis of the fiber optic segment is reflected by the beveled end surface at an angle that is transverse to the longitudinal axis;
   inserting the sleeve and fiber optic segment into a tube section of a cap member;
   fusing an exterior surface of the sleeve to an interior surface of a bore of the tube section; and
   closing an end of the tube section that is adjacent the beveled end surface.

20. The method of claim 19, further comprising annealing the fused fiber optic segment, sleeve and cap member.

21. The method of claim 20, wherein annealing the fused fiber optic segment, sleeve and cap member comprises heating fused fiber optic segment, sleeve and cap member to a temperature of greater than 1000 degrees Centigrade.

22. The method of claim 19, wherein beveling a reflecting end of the fiber optic segment comprises beveling an end of the sleeve.

23. The method of claim 19, further comprising forming a chamfer at an opening to the bore of the sleeve.

24. The method of claim 19, further comprising forming a chamfer at an opening to the bore of a receiving end of the tube section that is opposite the closed end.

* * * * *